United States Patent
Smith et al.

(10) Patent No.: US 6,676,633 B2
(45) Date of Patent: Jan. 13, 2004

(54) INTRAVASCULAR ADMINISTRATION SET NEEDLE SAFETY DEVICE

(75) Inventors: A. David Smith, Ellerslie, GA (US); J. Steven Kenny, Avondale Estates, GA (US)

(73) Assignee: Horizon Medical Products, Inc., Manchester, GA (US)

( * ) Notice: Subject to any disclaimer, the term of this patent is extended or adjusted under 35 U.S.C. 154(b) by 0 days.

(21) Appl. No.: 10/281,285

(22) Filed: Oct. 24, 2002

(65) Prior Publication Data

US 2003/0083624 A1 May 1, 2003

Related U.S. Application Data (60) Provisional application No. 60/348,017, filed on Oct. 24, 2001.

(51) Int. Cl.[7] .................... A61M 5/00; A61M 5/32; A61M 25/00
(52) U.S. Cl. ............... 604/110; 604/174; 604/177; 604/263; 604/264; 604/272
(58) Field of Search .............. 604/93.01, 110, 604/116, 117, 162, 164.04, 164.07, 164.08, 165.03, 174, 177, 192, 197, 198, 263, 264, 272, 165.01, 165.02, 165.04

(56) References Cited

U.S. PATENT DOCUMENTS

| | | | | |
|---|---|---|---|---|
| 4,627,843 A | * | 12/1986 | Raines | 604/263 |
| 5,584,813 A | * | 12/1996 | Livingston et al. | 604/177 |
| 6,261,259 B1 | * | 7/2001 | Bell | 604/93.01 |
| 6,264,259 B1 | | 7/2001 | Fortune | 294/64.1 |
| 6,500,155 B2 | * | 12/2002 | Sasso | 604/177 |
| 6,537,255 B1 | * | 3/2003 | Raines | 604/177 |

* cited by examiner

Primary Examiner—Brian L. Casler
Assistant Examiner—Mark K Han
(74) Attorney, Agent, or Firm—Needle & Rosenberg, PC.

(57) ABSTRACT

An intravascular administration set with an integral needle safety device is disclosed. An elongate needle trap is pivotally affixed at a first end to a needle stick guard. A winged needle holder carrying a needle is received by the needle stick guard and the needle trap, and is adapted to be moved along the length of the needle trap from the first end toward a second end thereof. A needle guide hole is defined within the needle stick guard, and at least a portion of the needle shaft is passed through the guide hole. The guide hole is axially spaced from the axis of the needle such that the needle is offset with respect to the guide hole once the needle is withdrawn therefrom.

32 Claims, 9 Drawing Sheets

INTRAVASCULAR ADMINISTRATION SET NEEDLE SAFETY DEVICE

CROSS REFERENCE TO RELATED APPLICATIONS

This application claims priority to provisional U.S. Patent Application Serial No. 60/348,017, filed on Oct. 24, 2001, in the United States Patent and Trademark Office, which application is incorporated fully herein by this reference.

FIELD OF THE INVENTION

The invention relates in general to intravascular administration sets. More particularly, the invention relates to a needle safety device adapted for use with an intravascular administration set.

BACKGROUND OF THE INVENTION

The use of intravascular administration sets to access implanted ports in the art of drug therapy is well known. As known, the access port is implanted beneath the subcutaneous layers of a patient's skin and accessed by the intravascular administration set. This is accomplished by percutaneous needle insertion into the access port through a penetrable septum, or by other conventional or known means, and is accomplished by using a non-coring hypodermic needle, for example a Huber needle.

Intravascular administration sets are designed to provide duration access to the implanted port. The use of these devices reduces the trauma otherwise associated with multiple punctures of the venous system, or the inconvenience of an externalized catheter for patient treatment purposes. Accordingly, and as known, intravascular administration sets are oftentimes used to access implanted ports to facilitate frequent blood sampling, or provide for the delivery of medications, nutritions, blood products, and imaging solutions into the blood stream, or to a treatment site within the patient.

Intravascular administration sets are supplied as sterile devices, and are provided for single patient use only. They are available in a variety of materials, including PVC, and other plastics. The non-coring needles are typically formed of stainless steel. Intravascular administration sets are comprised, therefore, of a non-coring needle, a device to secure the needle to the skin after it is inserted into the port, usually wings made of plastic, tubing to transport the fluids, and a connecting device, usually a luer type of connector fitting, used to connect the set to the fluid delivery device, i.e., a syringe. A clamp is placed on the tubing to stop the flow of fluids, and an injection site may be added to the set to allow for the infusion of additional fluids other than those fluids which are administered from the luer fitting.

A major problem with the known intravascular administration sets, however, is accidental sharps injuries, also referred to as "needle sticks." These are usually caused when the port is de-accessed, i.e., when the needle is explanted. To remove the needle from the intravascular administration set, the health care worker places two fingers from their off hand on the skin above the port to stabilize the port, the health care worker then removing the non-coring needle from the port with the other hand. Some force is required to remove the needle from the septum of the access port such that when the needle exits the port the natural reaction is to stop the upward motion. The body overreacts however, to stop this upward motion, and the needle sometimes sticks the health care worker. This is commonly referred to as a rebound injury. Due to the fact that the needles have been exposed to the patient's blood, any blood borne pathogen from the patient may therefore be transferred to the health care worker during this type of injury.

What is needed, therefore, is a device that will prevent a sharps injury or an accidental needle stick to health care workers, and which will also reduce the opportunity for the transmission of communicable diseases while de-accessing the treatment needles from an access port.

SUMMARY OF THE INVENTION

The present invention is an intravascular administration set incorporating a needle safety device adapted to prevent accidental needle sticks to health care workers and others during needle explant from a patient.

In a first embodiment, the invention comprises a winged hub, a needle holder, and a safety handle. In preparation for needle explant, the safety handle of the device is raised from a first position in which it is positioned parallel to the surface of the winged hub into a position in which the safety handle is perpendicular with respect to the winged hub. The safety handle is provided with an elongate internal slot, channel or track that is constructed and arranged to align with and receive a correspondingly shaped fitting on the needle holder therein when the safety handle is in its explant, or upright, position.

In this embodiment, as the needle is withdrawn from an implanted subcutaneous access port, for example, a finger from the user's off hand will be used to hold the safety handle down using a flat finger tab or area formed at the distal end of the safety handle. Applying downward force on the handle holds the infusion set winged hub next to the patient's skin and secures the access port in position around the needle. The needle holder provides a handle for the needle to be pulled upwards, for example toward the distal end of the safety handle. The infusion set winged hub also has a guide hole through which the needle is passed as it is extracted from the access port. Due to the specific shape of the Huber point needle, and the positioning of the guide hole within the winged hub such that it is axially offset with respect to the axis of the needle, the guide hole will allow the needle to be extracted, but will not allow the needle to return through the guide hole defined within the winged hub.

Accordingly, as the needle holder is pulled upwards, the needle exits the septum of the access port and the patient's epidermal skin layer. Once the needle clears the skin layer it is offset with respect to the guide hole, and is thus captured by and within the track of the safety handle held by the user's off hand. The needle cannot thereafter be re-extended, nor can it be used once again. The needle safety device will therefore cover or otherwise render unusable the point of the needle when the access port is de-accessed in order to prevent an accidental needle stick.

In a second embodiment, the intravascular administration set comprises a needle stick guard, a winged needle holder, and a needle trap. In preparation for needle explant using this embodiment of the device, the needle trap of the device is raised from a first position in which it is positioned parallel to the surface of the winged needle holder into a second position in which the needle trap is positioned perpendicular with respect to the winged needle holder. The needle stick guard and the needle trap together define a continuous elongate internal slot, channel or track that will align with and receive a correspondingly shaped head or track member on the winged needle holder therein when the needle trap is in the explant, or upright, position.

As the needle is withdrawn from the access port, the index finger and the thumb from the user's off hand are used to hold the needle stick guard down. Applying a downward force on the needle stick guard holds the safety assembly next to the patient's skin and secures the port in position around the needle. The winged needle holder also functions as a handle for use in moving the needle upwards, for example toward the distal end of the needle trap. The needle stick guard has a guide hole defined therein and through which the needle is passed as it is extracted from the access port. Due to the specific shape of the Huber point needle and the off center position of the hinge points of the needle trap on the needle stick guard, such that the needle stick guard may be rotated or offset into a safe position about the end of the needle trap, the guide hole will allow the needle to be extracted, but will not allow the needle to return through the needle stick guard.

Accordingly, as the needle holder is pulled upwards, the needle exits the septum of the access port and the patient's epidermal skin layer. Once the needle clears the skin layer and the needle stick guard, the needle is entrapped by and within the needle trap while the needle stick guard is held by the user's off hand, and cannot thereafter be re-extended nor used. The needle safety device will capture or otherwise render unusable the point of the needle when the access port is de-accessed in order to prevent an accidental needle stick.

With this invention the intravascular administration set can be used for the infusion or withdrawal of fluids when an implanted port is accessed as with any other infusion set. A feature of this invention, however, is the reduced exposure of a health care worker to an accidental needle stick with a used needle.

It is, therefore, an object of the invention to provide an improved intravascular administration set with an integral needle safety device which will help to reduce the possibility of an accidental needle stick or blood contamination injuries to health care workers.

DETAILED DESCRIPTION

Referring now in detail to the drawings, in which like reference numerals indicate like parts throughout the several views, a first embodiment of an intravascular administration set needle safety device 1 is illustrated in FIGS. 1–8. Referring now to FIGS. 1–5, the first embodiment of the needle safety device comprises an elongate safety handle 2 that is conventionally pinned or pivotally affixed to a generally planar winged hub 3 so that the safety handle may be rotated about an axis into an upright position with respect to the winged hub. As known, the hub may be flexible or rigid to the degree, and as, desired. A needle holder 4, having a Huber point needle 5 therein, or any other desired type of needle, is configured such that an elongate track 18 (FIG. 6) defined by and within the safety handle, and extending in the lengthwise direction thereof will align with and allow the passage therein of a mating or correspondingly shaped track member 19 (FIG. 7) formed as a part of the needle holder.

Figure 3:
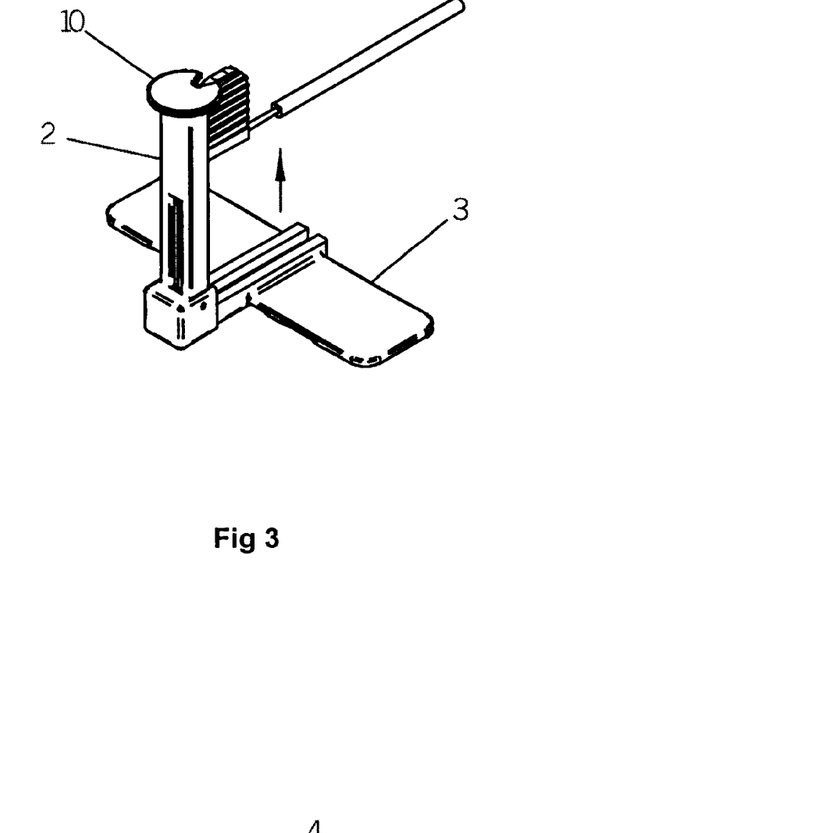
FIG. 3 is a perspective view of the needle safety device of FIG. 1 with the needle shown in the explant position.
Figure 4:
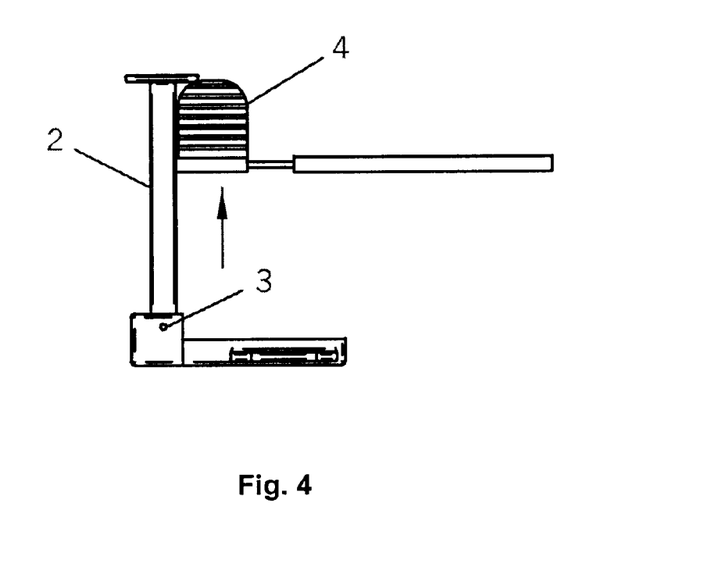
FIG. 4 is a side elevational view of the needle safety device of FIG. 1 with the needle shown in the explant position of FIG. 3.
Figure 5:
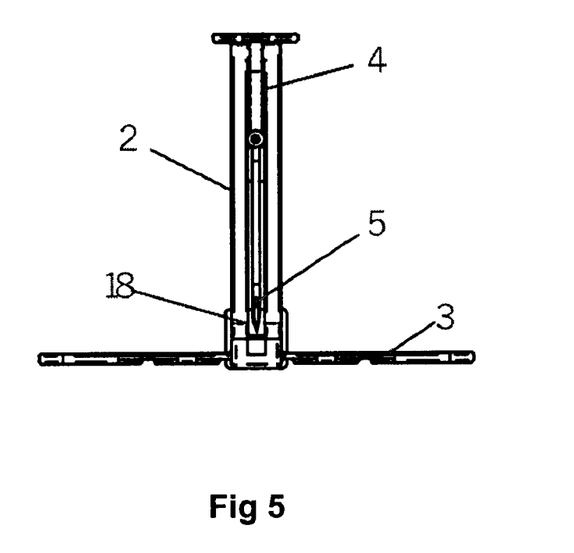
FIG. 5 is a rear elevational view of the needle safety device of FIG. 1 with the needle tip shown in the safe position.
Figure 6:
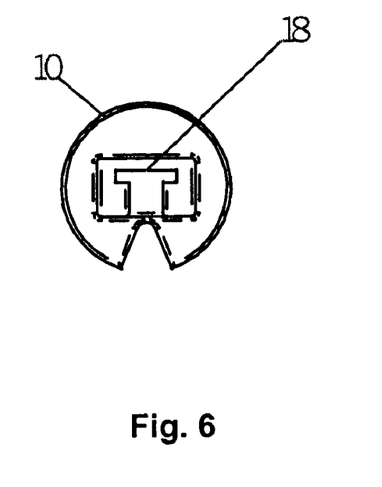
FIG. 6 is a top plan view of the safety handle of the needle safety device of FIG. 1 showing the elongate track or slot into which the needle holder will track.
Figure 7:
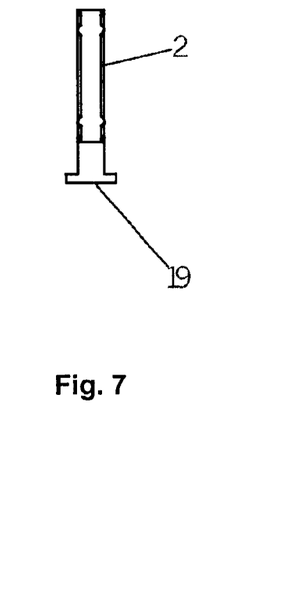
FIG. 7 is an end view of the needle holder of the needle safety device of FIG. 1 showing the track member defined on the needle holder for being received within the track shown in FIG. 6.
Figure 8:
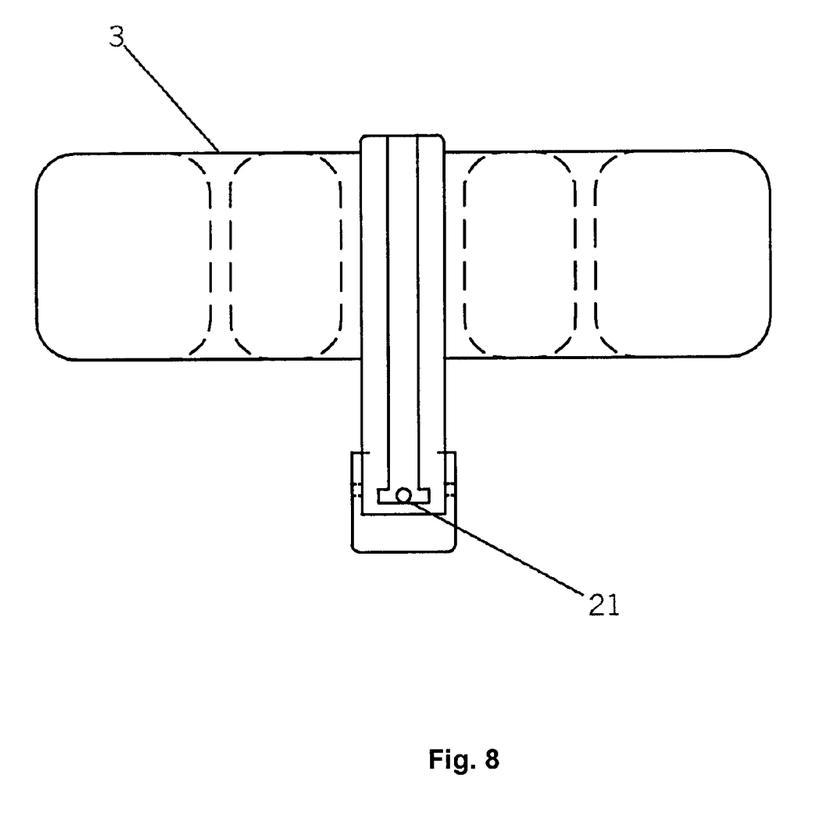
FIG. 8 is a top plan view of the winged hub of the needle safety device of FIG. 1.
Figure 9:
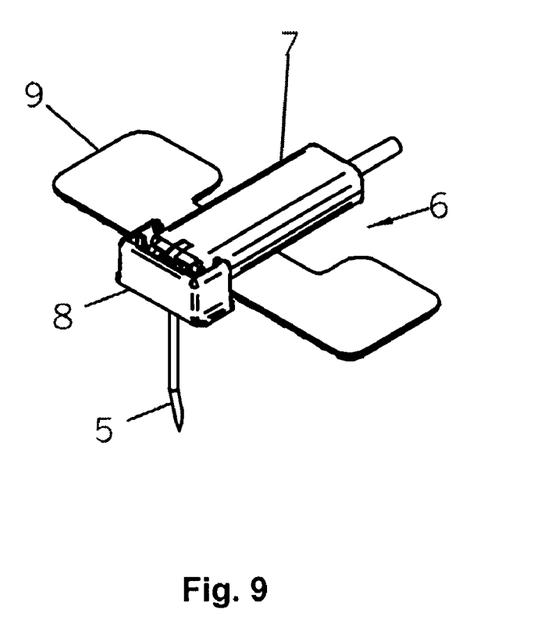
FIG. 9 is a perspective view of an intravascular administration set comprising a second embodiment of the needle safety device of the invention.

The needle holder, when fully retracted, or extracted, as shown in FIGS. 3–5, will stop positively against a top edge of the safety handle (FIG. 5). After the movement of the needle holder within the safety handle has stopped, the needle tip will be positioned above the winged hub and housed or captured securely within the track defined in the safety handle, as shown in FIG. 5. Additionally, the safety handle, in association with the needle holder received within the track 18 thereof, provides an indication that the needle safety device has been withdrawn or explanted properly. In this position, the needle tip cannot be touched nor can it be re-extended through the winged hub.

Figure 1:
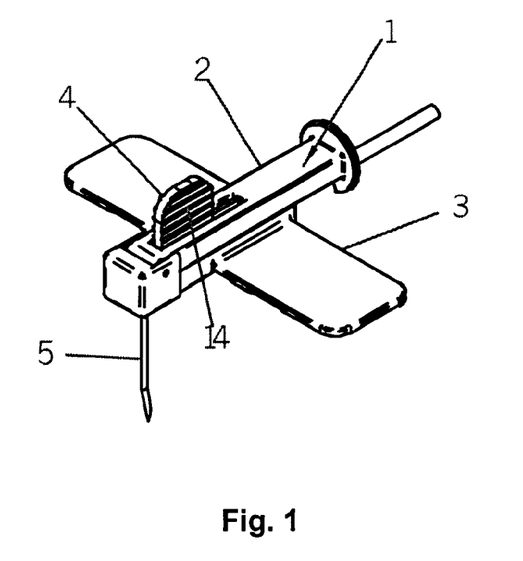
FIG. 1 is a perspective view of an intravascular administration set comprising a first embodiment of the needle safety device of the invention.
Figure 2:
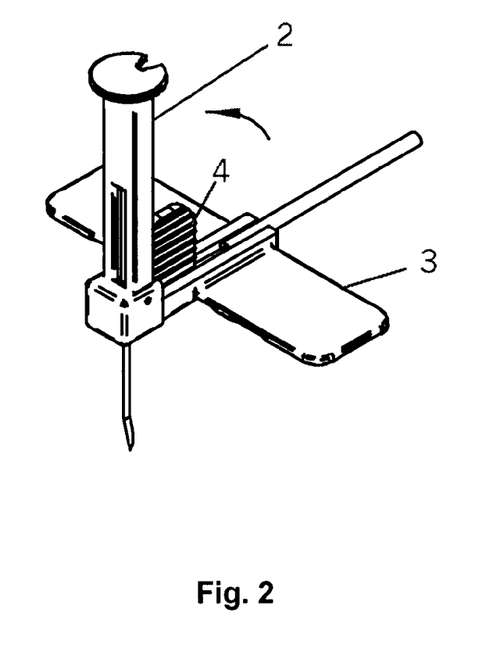
FIG. 2 is a perspective view of the needle safety device of FIG. 1 with the safety handle thereof shown in the needle explant position.

In use, the needle safety device, and in particular the Huber point needle, or any other desired and appropriate type of needle provided therewith, may be inserted normally into a septum (not illustrated) of a known type of an implant access port (not illustrated), which access port may comprise one of those known types of implantable access ports manufactured by Horizon Medical Products, Inc., for example, as would any other conventional intravascular administration or infusion set would be. This is accomplished with the safety handle and the needle holder positioned as shown in FIG. 1. To de-access or withdraw the needle from the access port, the safety handle of the device is rotated or raised through an angle of ninety degrees or so into the upright position shown in FIGS. 2–5. A finger (not illustrated) from the safety device user's off hand (not illustrated) is placed on a finger board 10 (FIG. 3) formed at the top of the safety handle to stabilize the bottom of the winged hub against the patient's skin surface (not illustrated) and the implanted access port. The user's strong hand (not illustrated) is used to grasp a tab 14 provided as a part of the needle holder, and used to pull the needle handle, and in turn the needle 5 from out of the septum of the implanted access port.

As the needle holder is raised or withdrawn from the access port, the track member 19 of the needle holder enters the track 18 defined in the safety handle, and thereafter tracks upwards along the length of and within the safety handle. As the needle clears the septum of the access port and the surface of the patient's skin, a needle guide hole 21 (FIG. 8) defined within the winged hub, allows the needle to pass upwardly therethrough. The needle guide hole is specifically sized to each gauge of Huber, or other type, of needle used with that intravascular administration set. Due to the shape of the Huber point needle, for example, the downward motion of the needle is stopped by the winged hub, preventing the needle point from passing through the opening 21 and exiting the safety handle/winged hub assembly. This is also made possible by the needle guide hole being defined within the winged hub such that the guide hole is axially offset with respect to the longitudinal axis of the needle. Accordingly, once the needle point passes upwardly through the hole in the winged hub, the needle shape produces a spring-like action that causes the needle point to move away from, i.e., it is no longer axially aligned with, the needle guide hole.

After the safety handle of the device is extended and activated, any downward pressure of the needle holder will force the needle point into the winged hub. The finger from the user's off hand is thereafter removed from the finger board and the entire intravascular administration set, also referred to as an infusion set when used with implantable access ports, can be disposed of safely and properly with a limited chance of a sharps injury or needle stick occurring to the health care professional handling the set. The needle point, once withdrawn into the safety handle, is thus no longer exposed to the user of the safety device or others, for example cleaning personnel, and cannot be reused due to the design of the assembly.

A second embodiment of an intravascular administration set needle safety device 6 of the invention is illustrated in FIGS. 9–17. Referring now to FIGS. 9–14, the needle safety device 6 here comprises an elongate needle trap 7 which is conventionally hinged or pivotally affixed to a needle stick guard 8 such that the needle trap may be rotated about an axis and into an upright position with respect to a planar winged needle holder 9. The needle holder is provided with a Huber point needle 5, or any other suitable needle type, and is constructed such that a continuous elongate track 11 (FIG. 15) defined by and within the needle stick guard and the needle trap, and which extends in the lengthwise direction of the needle trap, is aligned with and allows the passage therethrough of a mating or corresponding track member 12 (FIG. 16) formed as a part of the winged needle holder.

Figure 13:
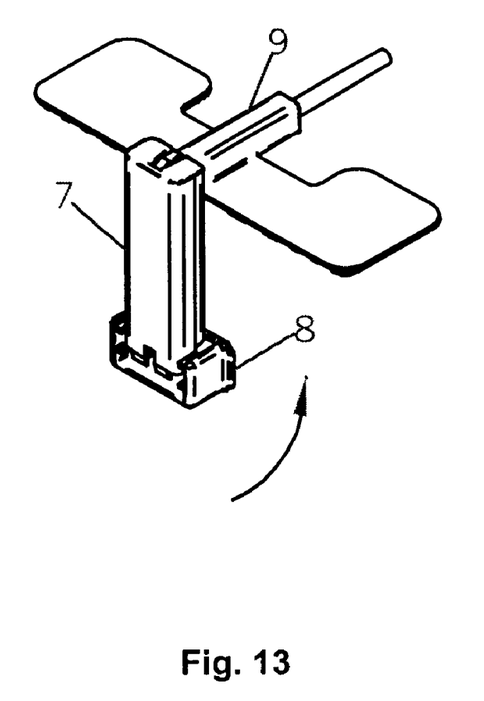
FIG. 13 is a perspective view of the needle safety device of FIG. 9 with the needle stick guard shown in the safe position about the end of the needle trap.
Figure 14:
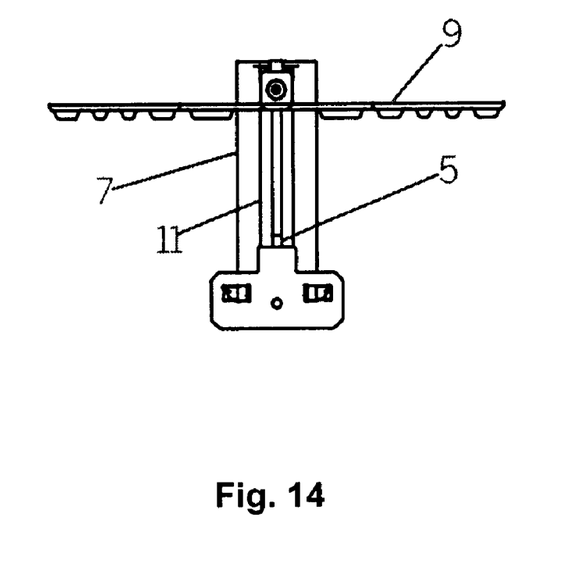
FIG. 14 is a rear elevational view of the needle safety device of FIG. 9 with the needle tip and needle stick guard shown in the safe position.
Figure 15:
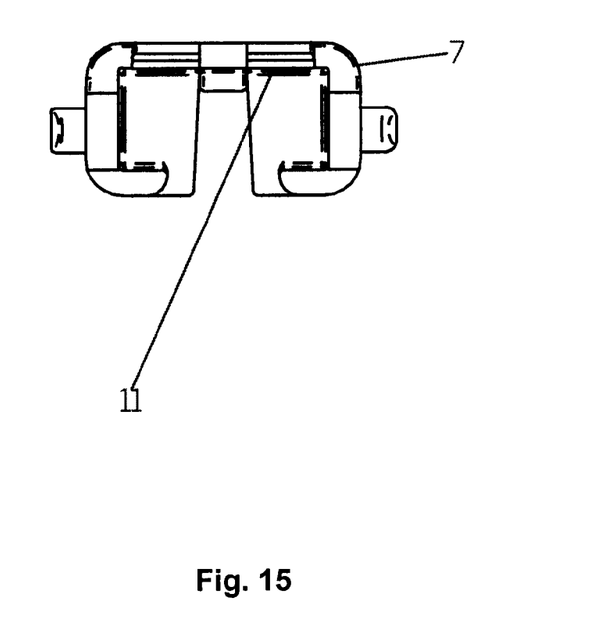
FIG. 15 is an end plan view of the needle trap of the needle safety device of FIG. 9 showing the elongate track or slot into which the winged needle holder is received.
Figure 16:
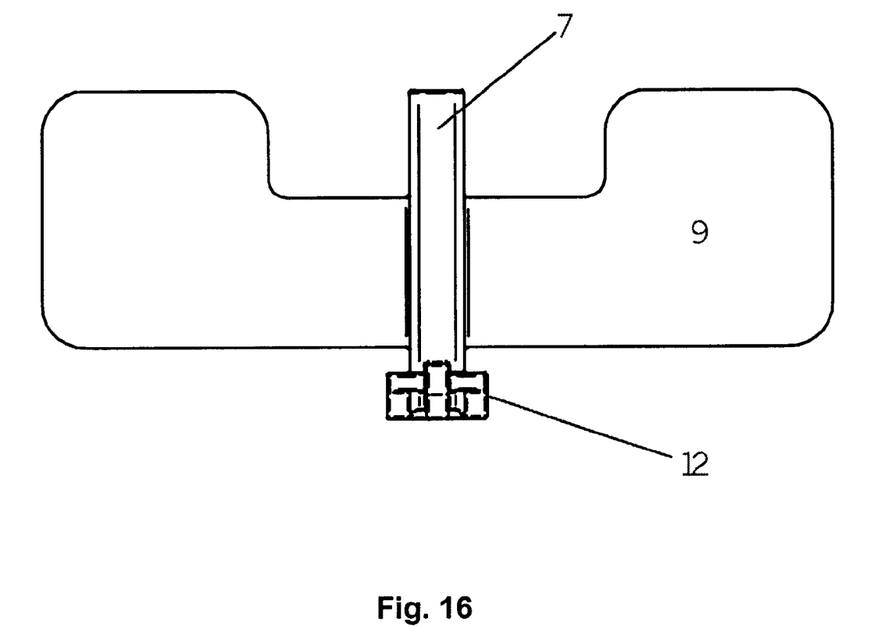
FIG. 16 is a top plan view of the winged needle holder of the needle safety device of FIG. 9 showing the track member defined on the needle holder for being received within the track shown in FIG. 15.
Figure 17:
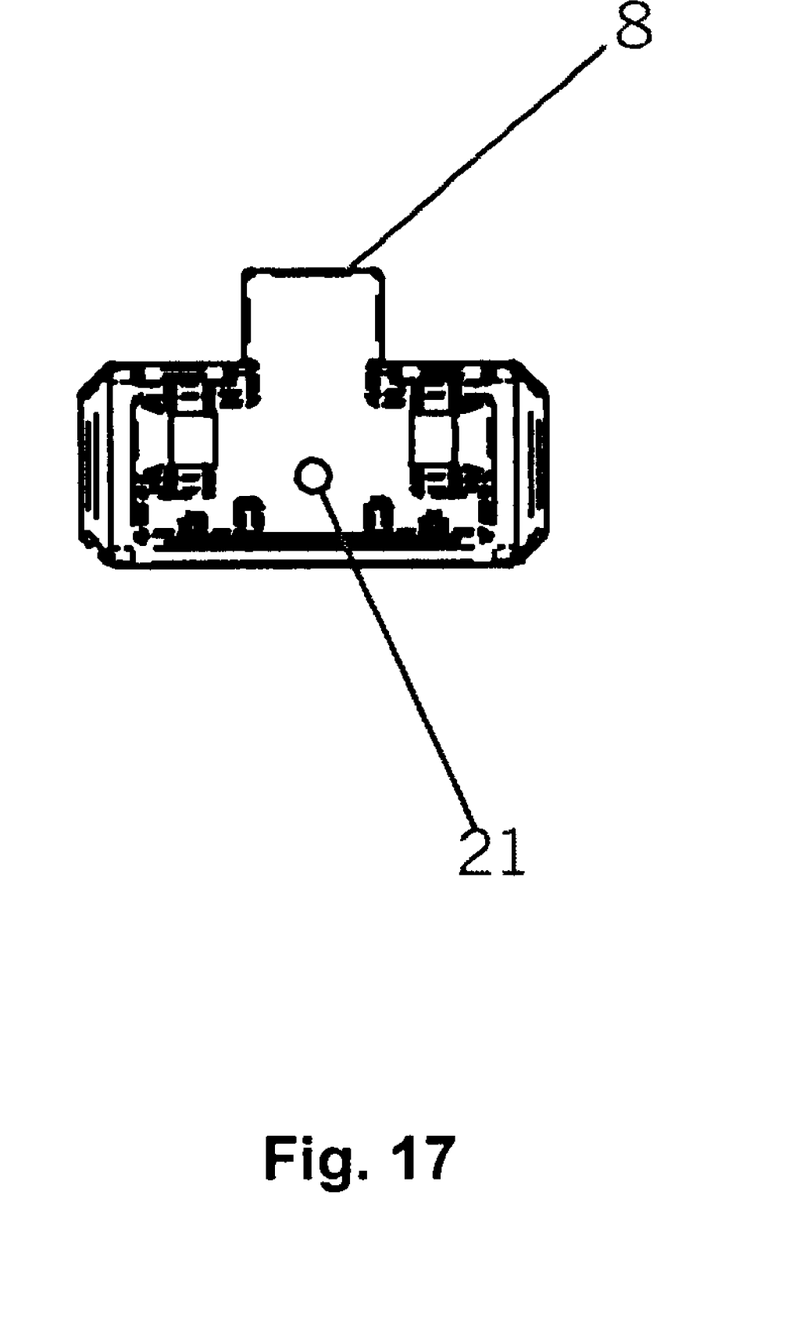
FIG. 17 is a top plan view of the needle stick guard of the needle safety device of FIG. 9.

The winged needle holder, when fully extracted as shown in FIGS. 11–14, will stop positively against a top edge of the needle trap and will be locked into a safe position, as shown in FIG. 14. After the winged needle holder has reached the full explant/safe position shown, the needle tip is captured within the track of the needle trap, and the needle stick guard may be pivotally rotated into a safe position enclosing the end of the needle trap through which the needle has been withdrawn to further guard the tip of the needle, as shown in FIGS. 13 and 14. A locking groove at the top of the needle trap and the movement of the needle stick guard into its position about the end of the needle trap, provide a visual indication that the needle safety device has been extended and secured properly. In this position, the needle tip is safely captured within the needle trap, more particularly the track 11 thereof, and cannot be touched nor extended through the needle stick guard. Additionally, the needle stick guard may be locked about the open end of the needle trap in a snap fit of known construction.

Figure 10:
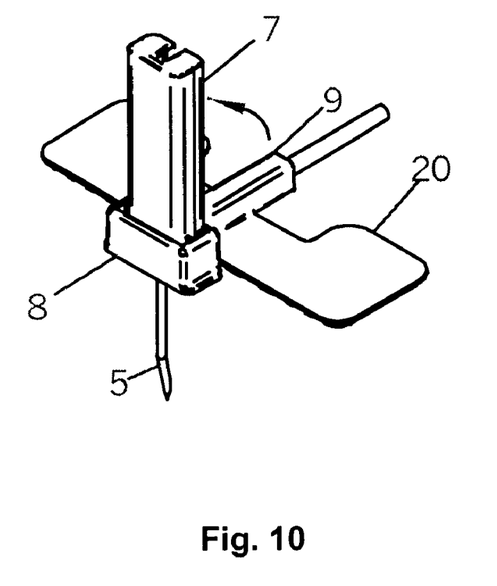
FIG. 10 is a perspective view of the needle safety device of FIG. 9 with the needle trap thereof shown in the needle explant position.
Figure 11:
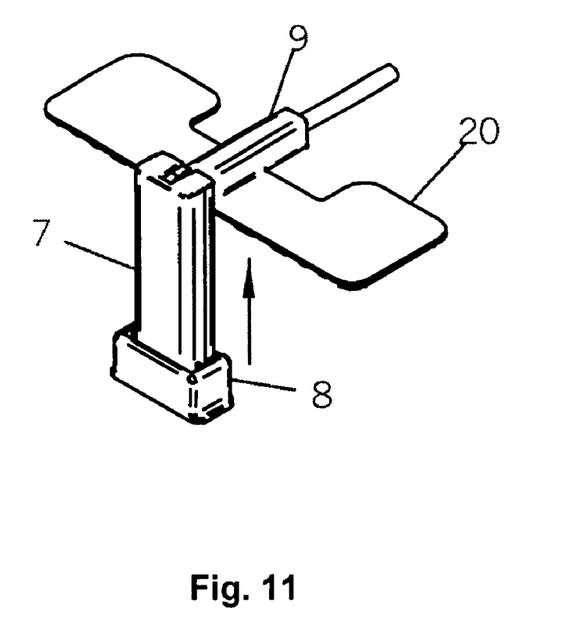
FIG. 11 is a perspective view of the needle safety device of FIG. 9 with the needle shown in the explant position.
Figure 12:
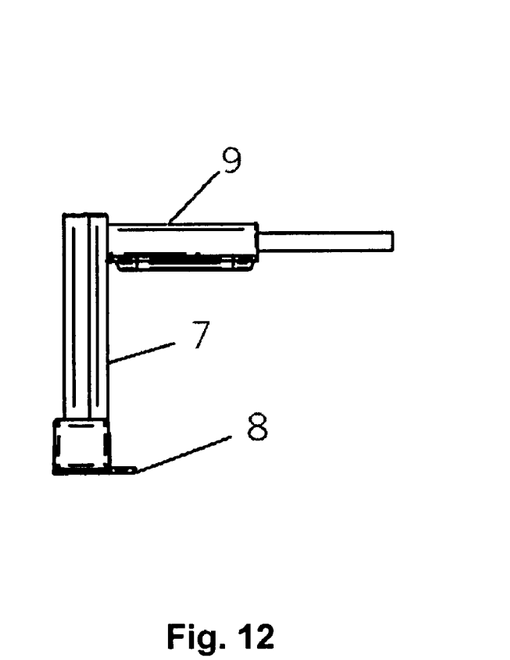
FIG. 12 is a side elevational view of the needle safety device of FIG. 9 with the needle shown in the explant position of FIG. 11.

To de-access or withdraw the second embodiment of the invention from an access port (not illustrated), the needle trap of the device is raised approximately ninety degrees into the upright position shown in FIG. 10. The index finger (not illustrated) and the thumb (not illustrated) from the user's off hand (not illustrated) are used to hold the needle stick guard 8 down against the patient's (not illustrated) skin (FIG. 10). Applying a downward force on the needle stick guard holds the administration set next to the patient's skin and secures the needle in the port about the needle tip. The user's dominant hand (not illustrated) grasps the wings 20 of the winged needle holder 9 which provide a handle for the needle to be pulled upwards and out of the access port, or the patient's vascular system, for example, and toward a distal end of the needle trap 7 (FIGS. 10, 11).

As the needle holder and its needle are withdrawn or explanted from the access port, the needle holder track member 12 (FIG. 16) of the winged needle holder enters the track 11 (FIG. 15) defined in the needle stick guard and the needle trap, and thereafter tracks upwards along the length of and within the needle trap. As the needle clears the septum of the access port and the surface of the patient's skin, a needle guide hole 21 (FIG. 17) defined within the needle stick guard 8, allows the needle to pass upwardly therethrough. The needle guide hole for the intravascular administration set is specifically sized to each gauge of Huber, or other type, of needle used. Due to the specific shape of the Huber point needle and the off-center positioning of the needle stick guard hinge points on the needle trap, the guide hole will allow the needle to be extracted as the needle is passed therethrough, but will not allow the needle to return through the needle stick guard once it rotates into its safe position shown in FIGS. 11–14. This is due to the fact that as the needle point passes upwardly through the guide hole in the needle stick guard, the bent needle shape produces a spring-like action that causes the needle point to move away from, i.e., it is no longer axially aligned with, the needle guide hole.

Accordingly, as the winged needle holder is pulled upwards, the needle exits the septum of the access port and the patient's epidermal skin layer. Once the needle clears the skin layer and the needle stick guard, the needle is captured by and within the track of the needle trap, and cannot thereafter be re-extended and the needle no longer used. For additional security the needle stick guard 8 can be locked into its safe position (FIGS. 13–14), for example by a snap fit construction. The needle safety device 6 will therefore cover or otherwise render unusable the point of the needle 5 once the access port is de-accessed in order to prevent an accidental needle stick or blood contamination accident.

After the device is activated and secured, any downward pressure will force the needle point into the needle stick guard. The fingers from the user's off hand are thereafter removed from the needle stick guard and the entire infusion set can be disposed of properly with no chance of a sharps injury or needle stick occurring. The needle point is thus no longer exposed to the user of the safety device or others, for example cleaning personnel, and cannot be reused due to the design of the assembly.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiment(s) disclosed herein, and that many modifications and other embodiments of the invention are intended to be included within the scope of the invention. Moreover, although specific terms are employed herein, they are used only in a generic and descriptive sense, and not for the purposes of limiting the described invention.

We claim:

1. An intravascular administration set with an integral needle safety device, comprising:
    a generally planar winged hub;
    an elongate handle pivotally affixed to the winged hub such that the handle can be moved from a first position in which the handle lies adjacent the hub into a second position in which the handle is extended away from the hub;
    a needle holder mounted to the handle, the needle holder having an elongate needle affixed thereto and extending away therefrom, the needle holder being constructed and arranged for movement at least partially in the lengthwise direction of the handle; and
    a needle guide hole defined within the hub, the needle holder having a first position in which at least a portion of the shaft of the needle is passed through the guide hole when the handle is in its first position, wherein the guide hole is axially spaced from the axis of the needle such that the shaft of the needle is offset with respect to the guide hole.

2. The device of claim 1, further comprising an elongate track defined within the handle and extending in the lengthwise direction thereof, the needle holder having a correspondingly shaped track member sized and shaped to be received within said track.

3. The device of claim 1, wherein the handle is positioned to be substantially perpendicular with respect to the hub in its second position.

4. The device of claim 1, the needle holder further comprising a planar grasping tab.

5. The device of claim 4, wherein said tab is extended through a slot defined in the handle when the handle is in its first position.

6. The device of claim 1, the handle further comprising a finger board positioned at an end of the handle spaced from the hub when the handle is in its second position.

7. The device of claim 1, the needle holder being constructed and arranged to be moved at least partially along the length of the handle when the handle is in its second position such that the needle holder may be moved into a second position spaced from the winged hub, the shaft of the needle being withdrawn from the guide hole in the second position of the needle holder.

8. The device of claim 7, wherein the guide hole is axially spaced from the axis of the needle such that the needle is offset with respect to the guide hole in the second position of the needle holder.

9. The device of claim 7, wherein the needle is captured within the handle in the second position of the needle holder.

10. The device of claim 7, wherein the needle cannot be re-extended through the guide hole when the needle holder is in its second position.

11. An intravascular administration set with an integral needle safety device, comprising:
    a needle stick guard;
    an elongate needle trap having a first end and a spaced second end, the needle trap being pivotally affixed at its first end to the needle stick guard;
    a generally planar winged needle holder received by the needle stick guard and the needle trap, the needle holder having an elongate needle affixed thereto and extending away therefrom;
    a needle guide hole defined within the needle stick guard, the needle holder having a first position in which at least a portion of the shaft of the needle is passed through the guide hole; and
    a continuous elongate track defined within the needle stick guard and the needle trap and extending in the lengthwise direction of the needle trap, the needle holder having a correspondingly shaped track member sized and shaped to be received within said track.

12. The device of claim 11, wherein the needle holder is constructed and arranged to be moved at least partially in the lengthwise direction of the needle trap.

13. The device of claim 11, the needle trap having a first position in which the needle trap lies adjacent the needle holder and a second position in which the needle trap is extended away from the hub.

14. The device of claim 13, wherein the needle trap is positioned to be substantially perpendicular with respect to the needle holder in its second position.

15. The device of claim 13, wherein the needle trap is positioned to be substantially perpendicular with respect to the hub in its second position.

16. The device of claim 13, the needle holder being constructed and arranged to be moved at least partially along the length of the needle trap from the first end toward the second end thereof when the needle trap is in its second position such that the needle holder may be moved into a second position spaced from the needle stick guard, the shaft of the needle being withdrawn from the guide hole in the second position of the needle holder.

17. The device of claim 16, wherein the guide hole is axially spaced from the axis of the needle such that the needle is offset with respect to the guide hole when the needle holder is in its second position.

18. The device of claim 16, wherein the needle is captured within the needle trap when the needle holder is in its second position.

19. The device of claim 16, wherein the needle cannot be re-extended through the guide hole when the needle holder is in its second position.

20. The device of claim 16, the needle stick guard being constructed and arranged to be pivotally moved on the first end of the needle trap once the needle holder is moved into its second position.

21. The device of claim 20, wherein the needle stick guard encloses the first end of the needle trap once pivoted about the first end thereof.

22. The device of claim 20, the needle stick guard being constructed and arranged to be received in a snap lock on the first end of the needle trap once the needle holder is moved into its second position.

23. The device of claim 11, wherein the guide hole is axially spaced from the axis of the needle such that the shaft of the needle is offset with respect to the guide hole.

24. An intravascular administration set with an integral needle safety device, comprising:

a generally planar winged hub;

an elongate handle pivotally affixed to the winged hub such that the handle can be moved from a first position in which the handle lies adjacent the hub into a second position in which the handle is extended away from the hub;

a needle holder mounted to the handle, the needle holder having an elongate needle affixed thereto and extending away therefrom, the needle holder being constructed and arranged for movement at least partially in the lengthwise direction of the handle; and a needle guide hole defined within the hub, the needle holder having a first position in which at least a portion of the shaft of the needle is passed through the guide hole when the handle is in its first position;

wherein the needle holder is constructed and arranged to be moved at least partially along the length of the handle when the handle is in its second position such that the needle holder may be moved into a second position spaced from the winged hub, the shaft of the needle being withdrawn from the guide hole in the second position of the needle holder;

and wherein the guide hole is axially spaced from the axis of the needle such that the needle is offset with respect to the guide hole in the second position of the needle holder.

25. A method of explanting a needle of an intravascular administration set from a patient, comprising the steps of:

pressing a generally planar winged hub of the intravascular administration set against the patient's skin to stabilize the set in position on the patient prior to needle explant;

moving an elongate handle pivotally affixed to the winged hub from a first position in which the handle lies adjacent the hub into a second position in which the handle is extended away from the winged member;

grasping a needle holder slidably mounted to the handle, the needle holder having the needle affixed thereto and extending away therefrom, and moving the needle holder out of a first position and at least partially in the lengthwise direction of the handle and away from the patient's skin; and withdrawing the shaft of the needle from a needle guide hole defined within the hub and axially offsetting the needle with respect to the guide hole as the needle is explanted from the patient.

26. The method of claim 25, comprising the step of passing the needle through the guide hole during the assembly of the intravascular administration set.

27. The method of claim 25, comprising the step of grasping a planar tab provided as a part of the needle holder when moving the needle holder at least partially in the lengthwise direction of the member and away from the patient's skin.

28. The method of claim 25, further comprising the step of capturing the explanted needle within the handle.

29. A method of explanting a needle of an intravascular administration set with an integral needle safety device from a patient, comprising the steps of:

pressing a generally planar winged needle holder of the intravascular administration set against the patient's skin to stabilize the set in position on the patient prior to needle explant;

moving an elongate needle trap pivotally affixed at a first end thereof to a needle stick guard from a first position in which the needle trap lies adjacent the needle holder into a second position in which the needle trap is extended away from the needle holder;

moving the needle holder within a continuous guide track defined by and within the needle stick guard and the needle trap, the needle holder having the needle affixed thereto and extending away therefrom, out of a first position and at least partially in the lengthwise direction of the needle trap and away from the patient's skin; and withdrawing the shaft of the needle from a needle guide hole defined within the needle stick guard and axially offsetting the needle with respect to the guide hole as the needle is explanted from the patient.

30. The method of claim 29, further comprising the step of capturing the explanted needle within the needle trap.

31. The method of claim 29, further comprising the step of pivotally rotating the needle stick guard about the first end of the needle trap to enclose the first end of the needle trap.

32. The method of claim 31, further comprising the step of pivotally rotating the needle stick guard into a snap lock on the first end of the needle trap.

\* \* \* \* \*